US00PP09407P

United States Patent [19]

McPheeters et al.

[11] Patent Number: Plant 9,407

[45] Date of Patent: Dec. 26, 1995

[54] 'EVERTHORNLESS' BLACKBERRY

[75] Inventors: Kenneth D. McPheeters; Robert M. Skirvin, both of Champaign, Ill.

[73] Assignee: Research Corporation Technologies Inc., Tucson, Ariz.

[21] Appl. No.: 390,617

[22] Filed: Feb. 17, 1995

Related U.S. Application Data

[63] Continuation of Ser. No. 760,781, Sep. 13, 1991, abandoned.

[51] Int. Cl.[6] ..... A01H 5/00

[52] U.S. Cl. ..... Plt./46.1

[58] Field of Search ..... Plt./46.1

[56] References Cited

U.S. PATENT DOCUMENTS

| | | | |
|---|---|---|---|
| P.P. 4,094 | 8/1977 | Doyle | Plt./46.1 |
| P.P. 6,101 | 2/1988 | Smith | Plt./46.1 |
| P.P. 6,105 | 2/1988 | Cox | Plt./46.1 |
| P.P. 6,678 | 3/1989 | Moore | Plt./46.1 |
| P.P. 6,679 | 3/1989 | Moore | Plt./46.1 |

OTHER PUBLICATIONS

K. McPheeters and R. M. Skirvin (1983), "Histogenic Layer Manipulation in Chimeral 'Thornless Evergreen' Trailing Blackberry", *Euphytica* 32 351–360.

Abstract 203, Session 34 (Jun. 1981) *HortScience* 16(3):426.

K. McPheeters and R. M. Skirvin (1989), "Somaclomal Variations Among Ex Vitro 'Thornless Evergreen' Trailing Blackberries", *Euphytica* 42: 155–162.

Master Thesis of Kenneth Dale McPheeters, Entitled Histogenic Layer Manipulation in Chimeral 'Thornless Evergreen' Trailing Blackberry, 1981.

Ph.D. Thesis of Kenneth Dale McPheeters, Entitled Stability of 'Thornless Evergreen' Blackberry In Vitro and Ex Vitro, 1985.

*Primary Examiner*—James R. Feyrer

*Attorney, Agent, or Firm*—Scully, Scott, Murphy & Presser

[57] ABSTRACT

This invention relates to a new and distinct trailing thornless blackberry cultivar named 'Everthornless', which is an ex vitro somaclonal variant of the 'Thornless Evergreen' cultivar of *Rubus laciniatus* Willd., that has good fruit yield and produces thornless, not thorny, shoots from its roots.

3 Drawing Sheets

This invention was made with government support under Hatch Act Funds awarded by the U.S. Department of Agriculture. The government has certain rights in the invention. This is a continuation of application Ser. No. 07/760,781, filed on Sep. 13, 1991, now abandoned.

SUMMARY OF THE INVENTION

The present invention relates to a new and distinct trailing thornless blackberry cultivar named 'Everthornless'. The 'Everthornless' blackberry cultivar, and ex vitro somaclonal variant of the 'Thornless Evergreen' cultivar of *Rubus laciniatus* willd., has good fruit yield, has a late ripening season and produces thornless, not thorny, shoots from its roots.

The 'Thornless Evergreen' is a periclinal chimera with a mutated thornless epidermal layer that encompasses internal cells which retain the genetic potential to produce thorns (technically, blackberry thorns are actually prickles that arise from epidermal tissue). As long as this periclinal arrangement is maintained, the plant stays thornless. However, any shoots arising from the internal tissue of a thorny genotype will be thorny and its gametes carry the thorny gene. Since blackberry roots develop from the thorny, internal parts of the stem, shoots coming from parental-type roots will always have thorns. Thorny canes interfere with cultural operations and harvest and may warrant abandonment of a planting.

The 'Thornless Evergreen' cultivar of *Rubus laciniatus* Willd., was introduced into shoot tip culture from virus-free plants. Shoot tips were proliferated and rooted in modified Murashige and Skoog plant tissue culture medium. These long-term cultures were used as research material for a project designed to identify an ex vitro nonchimeral thornless selection of 'Thornless Evergreen'.

Ex vitro plants of 'Thornless Evergreen' were examined for trueness to the original type. Adventitious buds from root segments were used to screen for presence of the thornless mutation in internal tissues. First-test field trial plantings were established in Urbana and Dixon Springs, Ill. and growth, flowering, and fruit set were monitored. Vegetative propagules of selections from Illinois first-test field trials were sent to Oregon State University, North Williamette Experiment Station, Aurora, Oreg. for second-test field trials.

From the second-test field trial, one somaclonal variant (a nonchimeral thornless plant) of 'Thornless Evergreen' was selected based on its growth and fruitfulness. This selection is named 'Everthornless'. The 'Everthornless' produces thornless advantitious shoots from roots and is compact (primocanes which are less than 3 meters in length compared to 'Thornless Evergreen' primocanes which are greater than 9 meters), which make it more suitable for the conventional trellising system of culture. Besides the shorter primocane length in the "Everthornless" cultivar, there are many other distinguishing features of the "Everthornless" cultivar relative to the parent "Thornless Evergreen" cultivar. Unlike the parent plant, the "Everthornless" cultivar produces thornless and not thorny shoots from its roots. In addition, the petioles of the "Everthornless" cultivar are quit different from the petioles of the parent "Thornless Evergreen". The petioles of the "Everthornless" cultivar are bent, a trait not found in the "Thornless Evergreen". Moreover, the "Thornless Evergreen" has clasping petioles that encircle the stem, while the petioles of the "Everthornless" have a swollen base, without the clasping petioles.

In addition, it has been surprisingly found that the "Everthornless" has almost twice as many prickles per leaf as the "Thornless Evergreen", as shown in the following Table:

TABLE 1

| Plant ID | Prickles/Leaf |
|---|---|
| "Thornless Evergreen" (n = 102) | 10.20 |
| "Everthornless" (n = 195) | 19.50 |

Furthermore, the "Everthornless" has more prickles near the base of the petioles than the "Thornless Evergreen", as shown in Table 2.

TABLE 2

| Plant ID | Mean Leaf Length (cm) | Length (cm) Q-1 + Q-2 | Length (cm) Q-3 + Q-4 | Mean Prickles Per Quadrant Q-1 | Q-2 | Q-3 | Q-4 |
|---|---|---|---|---|---|---|---|
| "Thornless Evergreen" | 12.60 | 2.21 | 4.09 | 1.1 | 2.1 | 5.4 | 2.1 |
| "Everthornless" | 11.55 | 2.11 | 3.61 | 2.8 | 3.2 | 9.0 | 4.5 |

In Table 2, the leaf was divided into four quadrants, with quadrant 1 (Q-1) being the base half of the petiole, quadrant 2 (Q-2) being the upper half of the petiole, quadrant 3 (Q-3) being the lower half of the midrib of the terminal leaflet and quadrant 4 (Q-4) being the tip half of the midrib of the terminal leaflet. As clearly shown by the data in Table 2, there were significantly more prickles in Q-1, Q-3 and Q-4 of the "Everthornless" relative to the corresponding quadrants in the parent "Thornless Evergreen".

However, upon closer examination, it was found that the majority of prickles were rudimentary and either so small or soft that they were negligible.

For purposes of evaluation, prickles were classified into the following types:

1. Full prickle (hard, recurved)
2. Soft prickle (fully formed, but not hard)
3. Aborted prickle (not fully formed)
4. Blister (elongated, raised area on epidermis)
5. Bump (small, round raised area on epidermis)

The thorny prickles are in the first classification.

Table 3 compares the prickle type distribution of the "Thornless Evergreen" and the "Everthornless".

TABLE 3

| | Mean number of prickles of each type per leaf quadrant | | | | | | | | | |
|---|---|---|---|---|---|---|---|---|---|---|
| | Q1(Petiole proximal 1/2) | | | | | Q2(Petiole distal 1/2) | | | | |
| Plant ID | 1 | 2 | 3 | 4 | 5 | 1 | 2 | 3 | 4 | 5 |
| "Thornless Evergreen" | 0.0 b | 0.0 | 0.1 b | 0.0 | 0.2 b | 0.0 b | 0.0 | 0.8 b | 0.0 | 0.8 a |
| "Everthornless" | 0.0 b | 0.0 | 0.7 ab | 0.0 | 1.0 a | 0.0 b | 0.0 | 1.7 a | 0.0 | 0.4 ab |

| | Mean number of prickles of each type per leaf quadrant | | | | | | | | | |
|---|---|---|---|---|---|---|---|---|---|---|
| | Q3(Midrib proximal 1/2) | | | | | Q4(Midrib distal 1/2) | | | | |
| Plant ID | 1 | 2 | 3 | 4 | 5 | 1 | 2 | 3 | 4 | 5 |
| "Thornless Evergreen" | 0.0 b | 0.0 | 3.5 b | 0.1 b | 0.7 b | 0.2 b | 0.0 b | 2.4 bc | 0.9 b | 0.5 |
| "Everthornless" | 0.0 b | 0.3 | 6.7 a | 0.1 b | 1.4 b | 0.0 b | 1.2 a | 5.4 a | 0.2 b | 0.4 |

As clearly shown by the data in Table 3, the leaves of the "Everthornless" had more variability in prickle morphology than the "Thornless Evergreen". Moreover, the prickles in the "Everthornless" were mostly of types 2–5, the soft prickles.

Another distinguishing feature is the presence of rudimentary thorns at the base of the primocanes in the "Everthornless". More specifically, the "Everthornless" tends to have some prickles on the first few inches (e.g., about 18 inches) of growth after which they become thornless. In contrast, the "Thornless Evergreen" are of two types: 1) no prickles at all of 2) many prickles along the entire length of the canes.

Each one of the features described hereinabove individually or in combination can be used to distinguish the "Everthornless" from its parent, the "Thornless Evergreen".

Furthermore, the fruits of the "Everthornless" are borne abundantly, but they are different from the "Thornless Evergreen". Although their shapes and appearances are similar, their tastes are quite different as shown in Table 4.

TABLE 4

| Plant ID | Berry Size[a] (g) | Normal Fruit % | pH | Acidity[b] % (w/w) | Soluble Solids % (w/w) |
|---|---|---|---|---|---|
| "Thornless Evergreen" | 3.0 | 95.0 ab | 3.30 a | 1.29 b | 13.6 ab |
| "Everthornless" | 3.5 | 97.0 b | 3.75 b | 0.80 a | 14.5 c |

[a]average weight of 25 berries/plot/harvest
[b]expressed as citric acid

As clearly shown by the data in Table 4, the "Everthornless" is less acidic and has a higher pH than the parent; moreover its sugar (soluble solid) content is significantly higher. Thus, the "Everthornless" is producing a superior quality fresh fruit product. However, the 'Everthornless' appears to be more winter hardy than the 'Thornless Evergreen'.

Characteristics such as good fruit yield, less vigorous cane growth and nonchimeral thornlessness render the 'Everthornless' a replacement cultivar for blackberry production in the Pacific Northwest and, in particular, for older 'Thornless Evergreen' plants which have become or are about to become overrun with thorny shoots from roots.

BRIEF DESCRIPTION OF THE DRAWINGS

The accompanying drawings are color photographs illustrating the new cultivar, including foliage and fruit. The color in each photograph is as nearly true as is reasonably possible to make in a color illustration of this character. The drawing comprises three sheets of photographs showing the plant of this invention in which:

Sheet 1 depicts substantially an entire specimen of the claimed plant in side view, in the field at a stage of ripeness for optimum harvest; with the cane attitude, poise of the foliage of the canopy, and fruit depicted in its characteristic, fairly uniform range of maturity;

Sheet 2 shows, in close range, the fruiting habit, with separated berries positioned in close proximity to a typical bearing lateral, with a close view of the top and bottom surfaces of leaflets, characteristic leaf stem structure, sepals, fruit cluster with attached ripe fruit; and, Sheet 3, illustrates a primocane and a bearing stem at fairly close range, with a central market container partially filled with harvested fruit.

DETAILED DESCRIPTION OF THE NEW VARIETY

The following is a detailed description of the pomological characteristics of the subject blackberry. Color identification is in accordance with the Royal Horticultural Society Colour Charts, except where common terms of color definition are employed.

Where dimensions, sizes, colors and other characteristics are given, it is to be understood that such characteristics are approximations of averages set forth as accurately as possible.

The descriptions reported herein are from the specimens group at Oregon State University, North Williamette Experiment Station, Aurora, Oreg., unless otherwise noted.

THE PLANT

Classification:
- *Botanical.*—*Rubus laciniatus* — 'Everthornless'.
- *Tradename.*—'Everthornless' blackberry.

Size: Long canes, trailing.
Growth: Vigorous, prolific suckering from crowns.
Cold hardiness: Medium to low; similar to 'Thornless Evergreen'.
Canes:
- *Description.*—Trailing; scattered rudimentary prickles at cane base.
- *Diameter.*—At 24" in height, range=0.72 to 1.74 cm.; average=1.20 cm.
- *Inernode length.*—4.8 cm.
- *Floricane color.*—Variable — 166A or 146C.
- *Date of primocane emergence.*—Approximately early May.
- *Foliage.*—Leaves: Deeply lacinate, palmately compound. Description: Average leaf has 14.7 leaflets. Mature leaf diameter: 12.7 cm. Length: 15.0 cm. Primocane leaf color: Adaxial: 137A. (Underside) abaxial: 147 B. Petioles: Rudimentary prickles, 8 per midrib. Length: 6.4 cm. Color: Adaxial: 166A. Abaxial: 145A.

THE FLOWER

Blooming habit:
- *Date of first bloom.*—Approximately mid-late June.
- *Date of last bloom.*—Approximately early August.

Blossom color:
- *Newly-opened.*—65C.
- *Fully-opened.*—56D.

Inflorescence form and size: Many branched cymose inflorescence.

Floret:
- *Number.*—15–21 flowers per lateral.
- *Form.*—Racemose cluster (at end of lateral).
- *Size.*—Lateral: 6–10" long.

Petals:
- *Number.*—6.
- *Texture and appearance.*—Smooth (typical Rubus flower).
- *Color.*—Newly-opened: 65C. Fully-opened: 56D.
- *First floret to open.*—Apical bud opens first and other buds open at random.

REPRODUCTIVE ORGANS

Staminodes: None.
Petaloid stamens: None.
Pistil:
- *Number.*—Range=40 to 60.
- *Length.*—3–6 mm long.
- *Stigma.*—Range=40 to 60.
- *Style.*—Range=40 to 60.
- *Ovary.*—One per stigma.

THE FRUIT

Maturity:
- *Description.*—Fruits on each lateral do not all mature at the same time.
- *Average first ripe date.*—Approximately early to mid-August.
- *Average period of maturity.*—Approximately mid-August to late-September.

Size:
- *Description.*—Medium size; average berry=3.5 g; uniform.
- *Diameter.*—Primary fruit equator: Range=1.4 to 1.8 cm; average=1.5 cm. Base pole: Range=1.7 to 2.2 cm; average=1.9 cm.

Shape: Somewhat conical.
Color: 202A.
Skin: Medium firm.
Drupelet size: Small.
Seed size: Medium; average 3.3 mg.
Firmness: Medium firm.
Flavor: Very good; mildly acid.
Soluble solids: 14.5%.
pH: 3.75.
Total acids: 0.80%.
Processed quality: Very good; comparable to the 'Thornless Evergreen'.
Uses: Fresh and processed; jellies; jam.

THE VARIETY

The most distinctive character of the variety is that it produces thornless, not thorny, root suckers.

What is claimed:

1. A new and distinct cultivar of blackberry substantially as illustrated and described herein, characterized by its thornless root suckers.

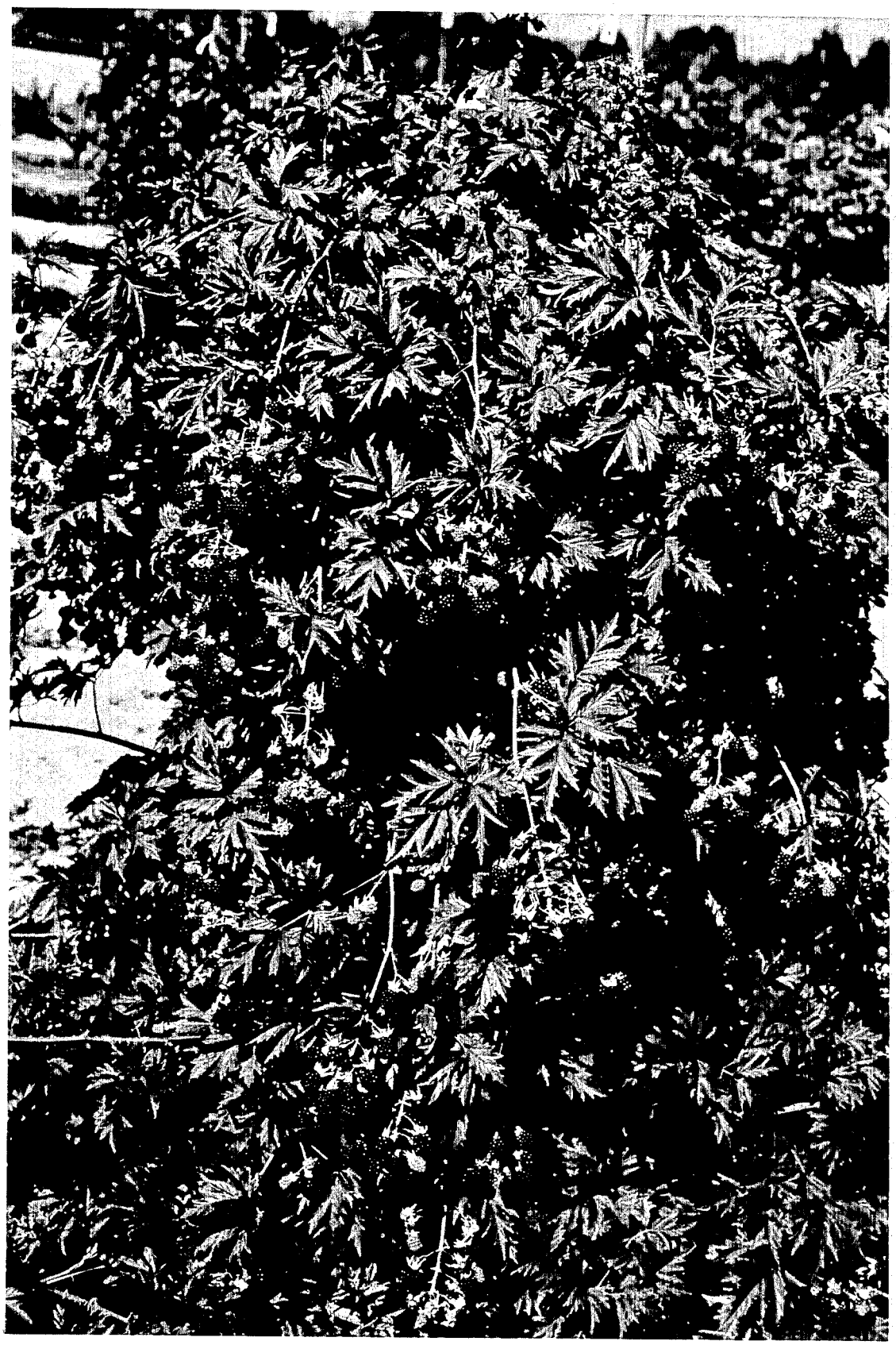

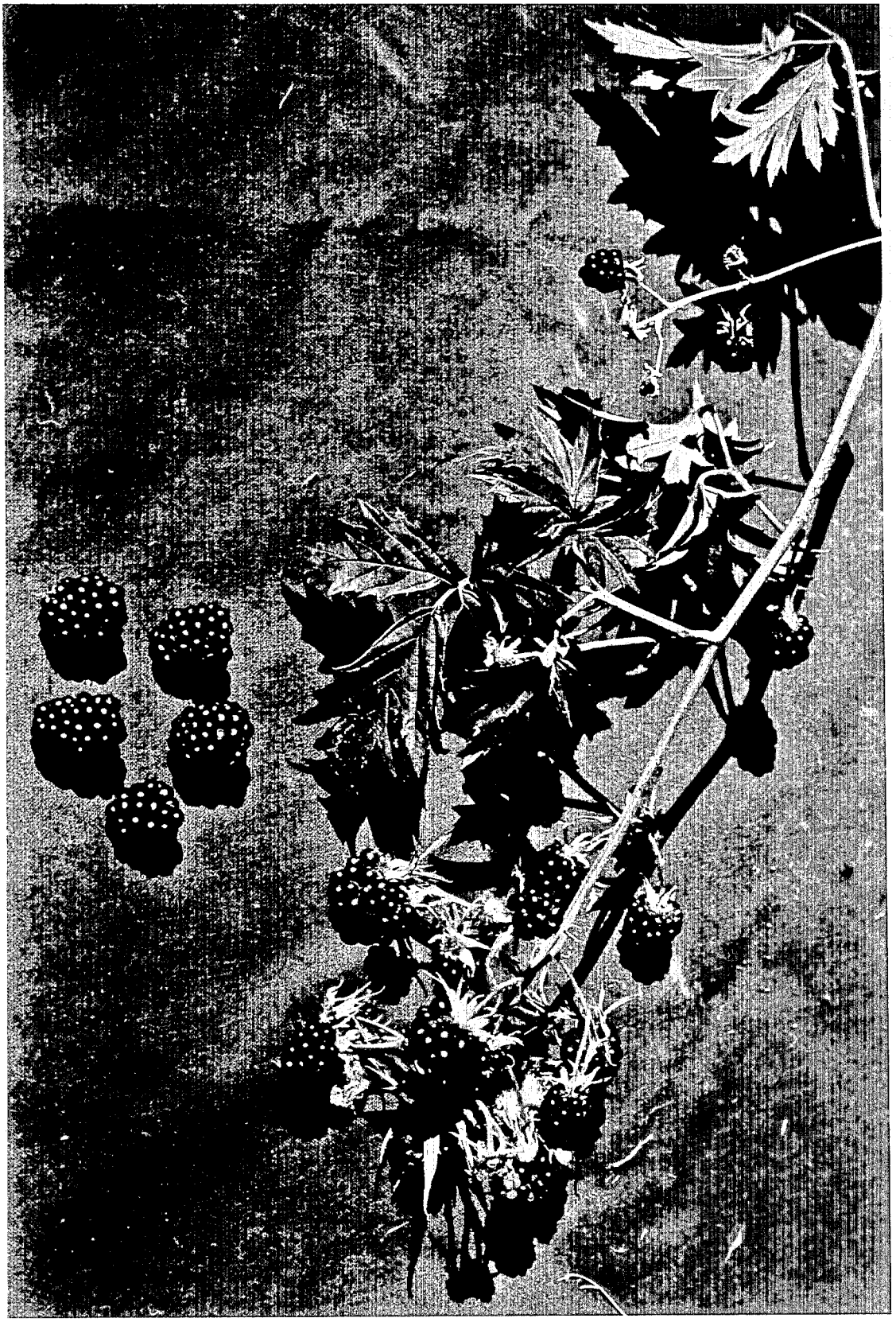

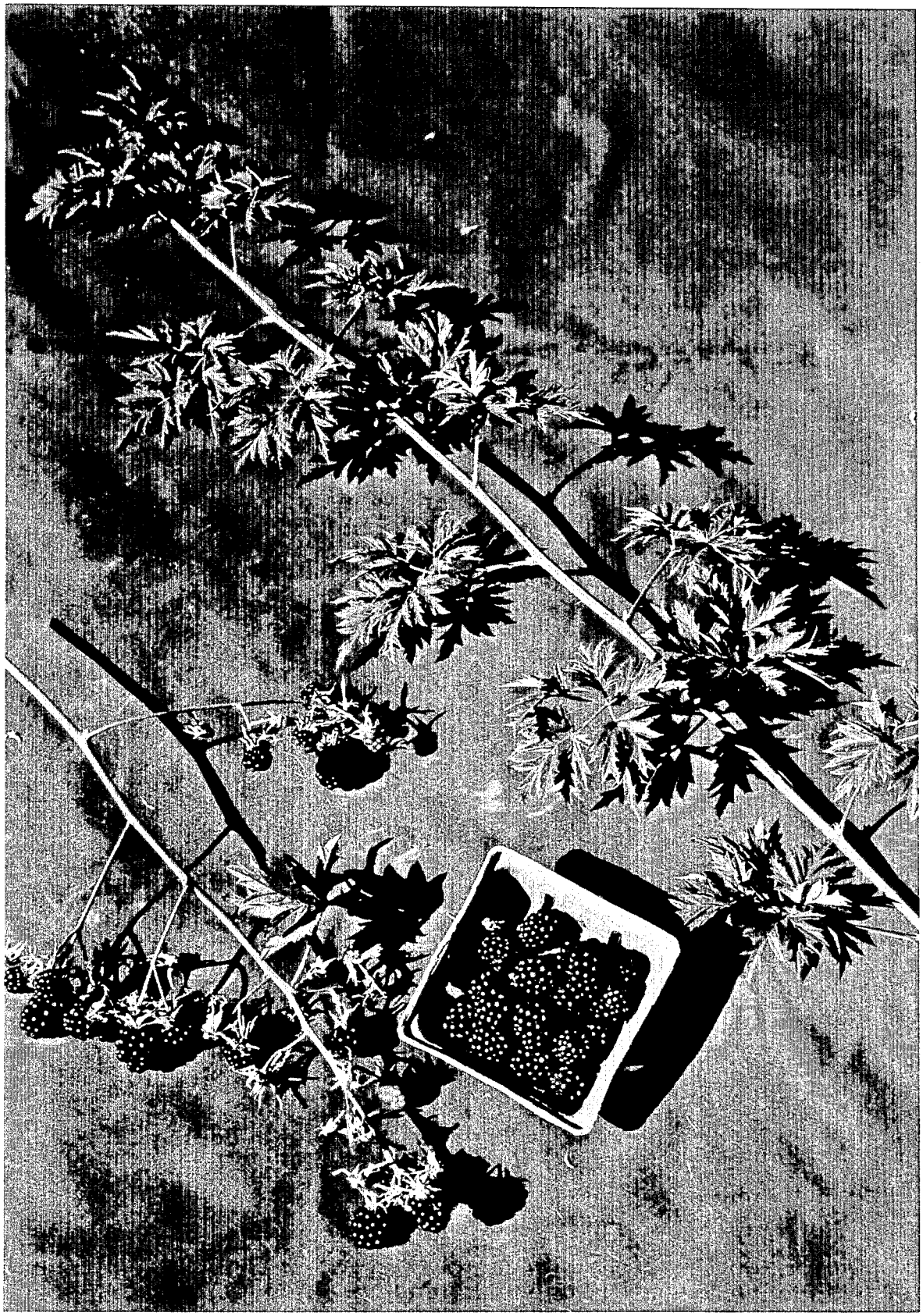

* * * * *